US00PP19225P2

(12) United States Plant Patent
van Haaster

(10) Patent No.: US PP19,225 P2
(45) Date of Patent: Sep. 16, 2008

(54) ***DAHLIA* PLANT NAMED 'CHALLENGING GLOW'**

(50) Latin Name: *Dahlia hybrida*
Varietal Denomination: Challenging Glow

(75) Inventor: Johanna G. H. van Haaster, Hillegom (NL)

(73) Assignee: Fides B.V., De Lier (NL)

( * ) Notice: Subject to any disclaimer, the term of this patent is extended or adjusted under 35 U.S.C. 154(b) by 81 days.

(21) Appl. No.: 11/633,117

(22) Filed: Dec. 1, 2006

(51) Int. Cl.
*A01H 5/00* (2006.01)

(52) U.S. Cl. ..... Plt./321
(58) Field of Classification Search ..... Plt./321
See application file for complete search history.

*Primary Examiner*—Howard J Locker
(74) *Attorney, Agent, or Firm*—C. A. Whealy

(57) ABSTRACT

A new and distinct cultivar of *Dahlia* plant named 'Challenging Glow', characterized by its upright, outwardly spreading and mounded plant habit; freely branching growth habit; freely flowering habit; large inflorescences with red-colored bright ray florets; and good postproduction longevity.

1 Drawing Sheet

Botanical designation: *Dahlia hybrida.*
Cultivar denomination: 'Challenging Glow'.

BACKGROUND OF THE INVENTION

The present invention relates to a new and distinct cultivar of *Dahlia* plant, botanically known as *Dahlia hybrida,* and hereinafter referred to by the name 'Challenging Glow'.

The new *Dahlia* is a product of a planned breeding program conducted by the Inventor in Lisse, The Netherlands. The objective of the breeding program is to create new pot-type *Dahlia* cultivars that have a freely branching and flowering habit, attractive ray floret coloration, and good post-production longevity.

The new *Dahlia* originated from an open-pollination in Lisse, The Netherlands of two unnamed selections of *Dahlia hybrida,* not patented. The new *Dahlia* was discovered and selected by the Inventor as a single flowering plant within the progeny of the stated open-pollination in a controlled environment in Lisse, The Netherlands in 2004.

Asexual reproduction of the new *Dahlia* by cuttings in a controlled environment in Lisse, The Netherlands, has shown that the unique features of this new *Dahlia* are stable and reproduced true to type in successive generations.

SUMMARY OF THE INVENTION

The cultivar Challenging Glow has not been observed under all possible environmental conditions. The phenotype may vary somewhat with variations in environment such as temperature and light intensity, without, however, any variance in genotype.

The following traits have been repeatedly observed and are determined to be the unique characteristics of 'Challenging Glow'. These characteristics in combination distinguish 'Challenging Glow' as a new and distinct cultivar of *Dahlia:*

1. Upright, outwardly spreading and mounded plant habit.
2. Freely branching growth habit.
3. Freely flowering habit.
4. Large inflorescences with bright red-colored ray florets.
5. Good postproduction longevity.

Compared to plants of the parent selections, plants of the new *Dahlia* differ primarily in ray floret coloration and plant size.

Plants of the new *Dahlia* can be compared to plants of the *Dahlia* cultivar Sunny Glow, not patented. In side-by-side comparisons conducted in Lisse, The Netherlands, plants of the new *Dahlia* differed from plants of the cultivar Sunny Glow in the following characteristics:

1. Plants of the new *Dahlia* were larger than plants of the cultivar Sunny Glow.
2. Plants of the new *Dahlia* flowered earlier than plants of the cultivar Sunny Glow.
3. Ray florets of plants of the new *Dahlia* were bright red-colored whereas ray florets of plants of the cultivar Sunny Glow were yellow-colored.

BRIEF DESCRIPTION OF THE PHOTOGRAPH

The accompanying photograph illustrates the overall appearance of the new *Dahlia.* The photograph shows the colors as true as it is reasonably possible to obtain in colored reproductions of this type. Colors in the photograph may differ slightly from the color values cited in the detailed botanical description which accurately describe the colors of the new *Dahlia.* The photograph comprises a side perspective view of a typical flowering plant of 'Challenging Glow' grown in a container.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in a glass-covered greenhouse in De Lier, The Netherlands during the winter and early spring and under conditions and practices which approximate those generally used in commercial *Dahlia* production. During the production of the plants, day and night temperatures averaged 18° C. Measurements and numerical values represent averages for typical flowering plants. Plants were about 10 weeks from planting when the photograph and description were taken.

Botanical classification: *Dahlia hybrida* cultivar Challenging Glow.

Parentage:

*Female, or seed, parent.*—Unnamed selection of *Dahlia hybrida,* not patented.

*Male, or pollen, parent.*—Unnamed selection of *Dahlia hybrida,* not patented.

Propagation:

*Type.*—By cuttings.

*Time to initiate roots, summer.*—About six days at temperatures of about 22° C.

*Time to initiate roots, winter.*—About eight days at temperatures of about 20° C.

*Time to produce a rooted young plant, summer.*—About 12 days at temperatures of about 22° C.

*Time to produce a rooted young plant, winter.*—About 16 days at temperatures of about 20° C.

*Root description.*—Fine, fibrous; tuber development has not been observed.

*Rooting habit.*—Freely branching; dense.

Plant description:

*Plant form/growth habit.*—Upright, outwardly spreading and mounded plant form; inverted triangle. Freely basal branching with about six primary branches each with numerous secondary branches and inflorescences held above the foliage on moderately strong peduncles; bushy and dense habit. Moderately vigorous growth habit.

*Plant height.*—About 23 cm.

*Plant diameter or spread.*—About 15 cm to 18 cm.

*Lateral branches* (*peduncles*).—Length: About 25 cm. Diameter: About 6 mm. Internode length: About 3.5 cm. Aspect: Erect to somewhat outwardly spreading. Strength: Moderately strong. Texture: Smooth, glabrous. Color: 144B.

Foliage description:

*Arrangement.*—Leaves opposite; leaves may be single or compound with three or five leaflets.

*Shape.*—Ovate.

*Apex.*—Acute.

*Base.*—Attenuate.

*Margin.*—Serrate.

*Leaflet length.*—About 6 cm.

*Leaflet width.*—About 4 cm.

*Venation pattern.*—Pinnate.

*Texture, upper and lower surfaces.*—Slightly pubescent.

*Color.*—Developing and fully expanded foliage, upper surface: 136A; venation, 146C. Developing and fully expanded foliage, lower surface: 138B; venation, 137C.

*Petiole length.*—About 1.5 cm to 2 cm.

*Petiole diameter.*—About 3 mm.

*Petiole texture, upper and lower surfaces.*—Smooth, glabrous.

*Petiole color, upper and lower surfaces.*—146C.

Inflorescence description:

*Appearance.*—Rotate single inflorescence form with ray and disc florets. Inflorescences positioned above the foliage on moderately strong peduncles. Inflorescences face upright to slightly outwardly. Freely flowering habit; about 20 inflorescences develop per plant. Inflorescences persistent. Inflorescences not fragrant.

*Time to flower.*—Plants flower continuously from late spring through the autumn in The Netherlands. Plants begin flowering about 6.5 weeks after planting.

*Post-production longevity.*—Inflorescences maintain good substance for about five to ten days on the plant.

*Inflorescence bud.*—Height: About 5 mm. Diameter: About 8 mm. Shape: Globular. Color: 144B to 144C.

*Inflorescence size.*—Diameter: About 5 cm to 5.5 cm. Depth (height): About 2.2 cm. Disc diameter: About 5 mm. Receptacle height: About 5 mm. Receptacle diameter: About 1.5 to 2 cm.

*Ray florets.*—Length: About 2 cm. Width: About 8 mm. Shape: Ovate. Apex: Obtuse. Base: Cuneate. Aspect: Initially upright to roughly perpendicular to the peduncle; concave. Texture, upper and lower surfaces: Smooth, glabrous; satiny. Number of ray florets per inflorescence: About 100 to 110 arranged in about seven to eight whorls. Color: When opening, upper surface: 43A. When opening, lower surface: 43A to 43C. Fully opened, upper surface: 34A; color becoming close to 34B with development. Fully opened, lower surface: 34C.

*Disc florets.*—Shape: Tubular; apex rounded. Length: About 1 cm. Diameter, apex: About 2 mm. Diameter, base: About 1 mm. Number of disc florets per inflorescence: About 10. Color: Immature: 15C. Mature: Apex: 14A. Mid-section: 17A. Base: 145C.

*Phyllaries.*—Quantity per inflorescence: About seven to nine arranged in a single whorl. Length: About 1 cm to 1.5 cm. Width: About 6 mm. Shape: Ovate. Apex: Acute. Base: Cuneate. Margin: Entire. Texture, upper and lower surfaces: Smooth, glabrous. Color, upper surface: 137B. Color, lower surface: 143B.

*Reproductive organs.*—Androecium: Quantity per disc floret: Five. Anther shape: Ovoid. Anther length: About 2.5 mm. Anther color: 14A. Pollen amount: Moderate. Pollen color: 17A. Gynoecium: Quantity per ray or disc floret: One. Pistil length: About 9 mm. Stigma shape: Lanceolate; flattened. Stigma color: 14A. Style length: About 8 mm. Style color: 7B. Ovary color: 1C. Seeds: Seed development has not been observed.

Disease/pest resistance: Plants of the new *Dahlia* have not been shown to be resistant to pathogens and pests common to *Dahlia.*

Garden performance: Plants of the new *Dahlia* have exhibited good tolerance to rain and wind and have been observed to tolerate temperatures from about 2° C. to about 30° C.

It is claimed:

1. A new and distinct *Dahlia* plant named 'Challenging Glow' as illustrated and described.

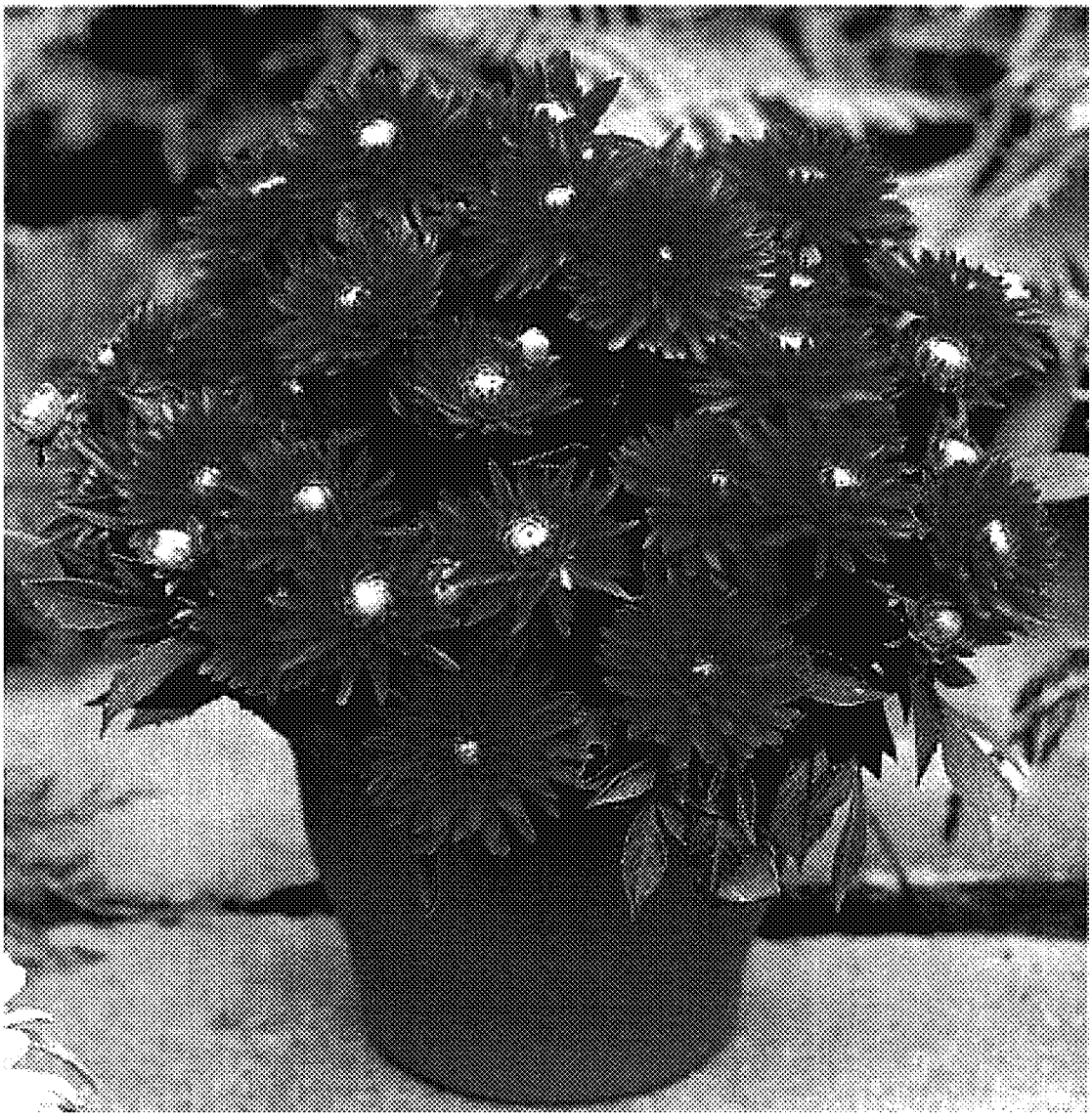

* * * * *